United States Patent [19]

Gonser

[11] 4,123,673
[45] Oct. 31, 1978

[54] CONTROL CIRCUIT FOR AN ELECTRICAL DEVICE

[75] Inventor: Donald I. Gonser, Forest Park, Ohio

[73] Assignee: Dentsply Research and Development Corporation, Milford, Del.

[21] Appl. No.: 777,077

[22] Filed: Mar. 14, 1977

[51] Int. Cl.² .............................................. A61B 17/36
[52] U.S. Cl. ................................ 307/326; 128/303.13; 128/303.14
[58] Field of Search ............................. 307/326, 327; 128/303.13, 303.14, 303.17; 361/173

[56] References Cited

U.S. PATENT DOCUMENTS

| | | | |
|---|---|---|---|
| 3,227,929 | 1/1966 | McCreight | 361/173 |
| 3,601,126 | 8/1971 | Estes | 128/303.14 |
| 3,952,748 | 4/1976 | Kaliher et al. | 128/303.14 |

Primary Examiner—Robert K. Schaefer
Assistant Examiner—M. K. Mutter
Attorney, Agent, or Firm—James W. Pearce; Roy F. Schaeperklaus

[57] ABSTRACT

A control circuit for an electrical device which includes a switch that is electrically isolated from other components. The switch is connected in series with a photovoltaic cell and relay means. The photovoltaic cell is illuminated so that closing of contacts of the switch causes actuation of the relay means. The relay means is connected to actuate the electrical device. Voltage at the switch is limited by the voltage produced by the photovoltaic cell.

8 Claims, 1 Drawing Figure

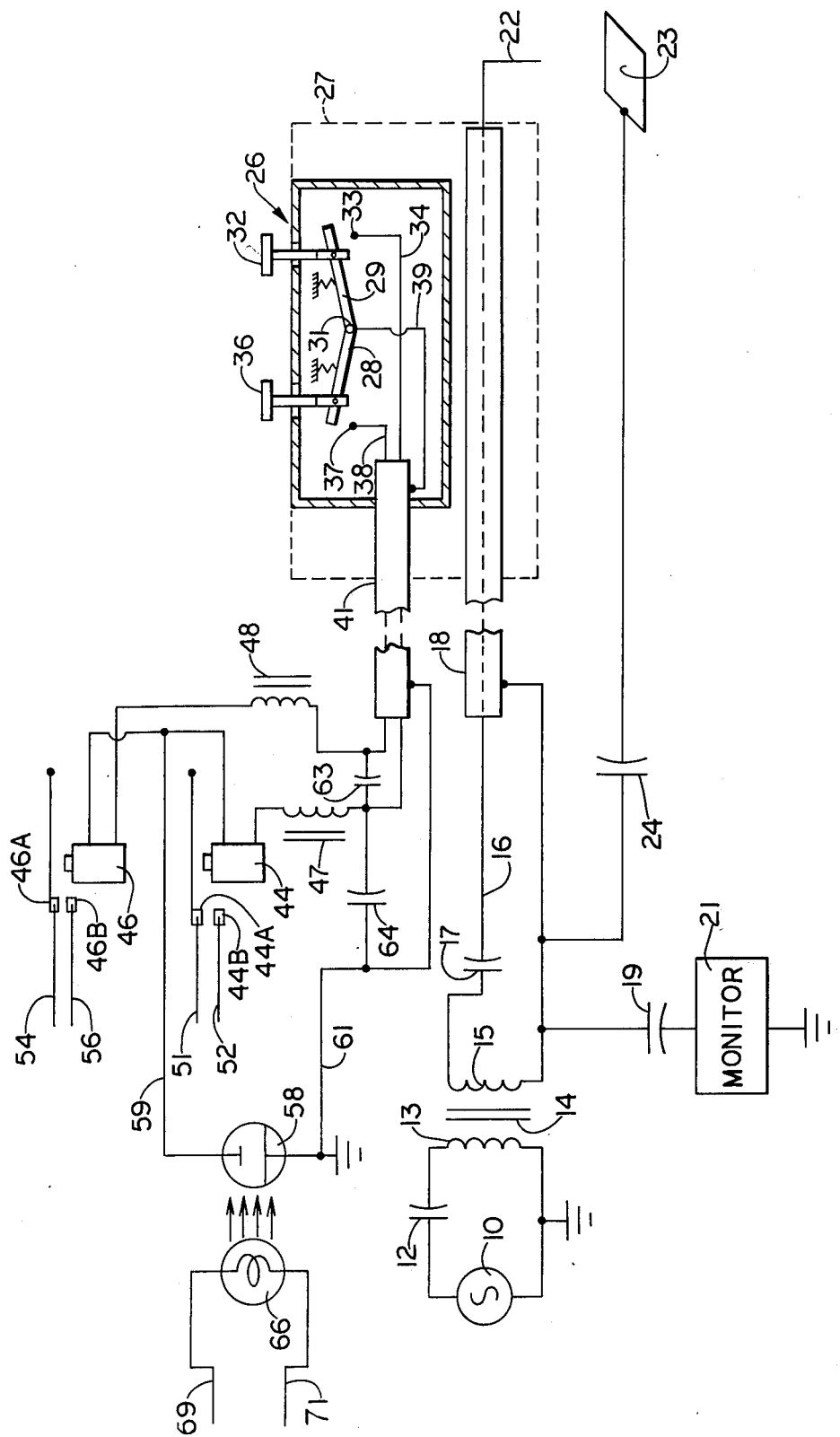

CONTROL CIRCUIT FOR AN ELECTRICAL DEVICE

This invention relates to electrical switching devices. More particularly, this invention relates to remote controlled switch devices.

In many types of electrical apparatus, it is necessary to isolate a switch from circuits controlled by the switch, and an object of this invention is to provide a switch device in which apparatus controlled by the switch is electrically isolated from the switch.

In radiofrequency electrosurgical devices and the like, it can be desirable to have a switch close to an active electrode as in a handpiece. However, if conventional switch leads carrying substantial currents extend to the handpiece, there is a danger of leakage of current from the switch leads to a switch actuator to cause burns and the like. A further object of this invention is to provide a switch for an electrosurgical device in which current in switch leads is limited to prevent such burning.

A further object of this invention is to provide a switch operated system which inherently limits the current which circulates in switch leads.

A further object of this invention is to provide a switch circuit in which power is supplied by circuits of the device controlled thereby but in which circuits of the device are fully isolated from the switch circuit.

Briefly, this invention provides a switch circuit in which a current for operating a relay or the like is supplied by a photovoltaic cell. The relay actuates auxiliary contacts which actuate a device controlled by the switch circuit. The photovoltaic cell can be powered by a radiating source or lamp which, in turn, can be powered by an appropriate electrical power source, which can be a portion of the device controlled by the switch circuit. The power circuits of the device are fully isolated from the photovoltaic cell because there is no direct connection therebetween, and the power circuits are similarly isolated from the leads which extend to the switch. The current supplied by the photovoltaic cell is limited by the electrical characteristics of the photovoltaic cell and inherently cannot exceed a given output voltage at optical saturation, which can be sufficiently low that there is limited potential danger if the voltage at the switch contacts reaches an operator. When the device controlled by the switch is an electrosurgical device, and the switch is in a handpiece, an active lead of the electrosurgical device can be shielded and can be closely related to ground so that there can be no substantial leakage of radiofrequency current from the active lead to the switch leads.

The above and other objects and features of the invention will be apparent to those skilled in the art to which this invention pertains from the following detailed description and the drawing, which is a schematic view showing a switch circuit constructed in accordance with an embodiment of this invention, the switch circuit being shown in conjunction with a radiofrequency electrosurgical device.

In the drawing is shown a circuit for a radiofrequency electrosurgical device which includes a radiofrequency generator 10 (not shown in detail). The radiofrequency generator 10 is coupled through a condenser 12 to a primary winding 13 of a coupling transformer 14. One side of a secondary winding 15 of the coupling transformer 14 is coupled to an active power lead 16 through a condenser 17. The active power lead 16 can be the inner or shielded conductor of a coaxial cable 18. The outer conductor or shield of the coaxial cable 18 is connected to a return side of the secondary winding 15 and through a condenser 19 and a monitor device 21 to ground. The monitor device can be of the type shown in my co-pending application Ser. No. 543,489 filed Jan. 23, 1975, and provides a low impedance path from the shield of the coaxial cable 18 to ground.

The active power lead 16 powers an active electrode 22. A passive electrode 23 is coupled to the return side of the secondary winding 15 through a condenser 24.

Operation of the radiofrequency generator 10 is controlled by a switch assembly 26 mounted in a handpiece 27 which supports the active electrode 22. The switch assembly 26 includes switch arms 28 and 29, which are carried on a shaft 31. The shaft 31 is pivotally mounted in appropriate bearings (not shown). When a push button 32 is depressed, the switch arm 29 engages a contact 33 to which a lead 34 is attached. When a push button 36 is depressed, the switch arm 28 engages a contact 37 to which a lead 38 is attached. A lead 39 is attached to the switch arms 28 and 29. The lead 39 is also attached to a tubular electrical shield 41. The leads 34 and 38 extend through the electrical shield 41.

The leads 34 and 38 are connected through radiofrequency inductances 47 and 48 to relay coils 44 and 46, respectively. The relay 44 includes contacts 44A and 44B, which are attached to leads 51 and 52, respectively. The leads 51 and 52 can be part of the control circuitry of the radiofrequency generator 10 (not shown in detail), which leads 51 to 52, when connected together, permit the radiofrequency generator to deliver a selected radiofrequency electrosurgical current, such as a cutting current, to the transformer 14, the active power lead 16 and the active electrode 22. The relay 46 includes contacts 46A and 46B, which are attached to leads 54 and 56, respectively. The leads 54 and 56 can be part of the control circuitry of the radiofrequency generator 10, which leads 54 and 56, when connected together, permit the radiofrequency generator to deliver another selected radiofrequency electrosurgical current, such as a coagulating current, to the transformer 14, the active power lead 16 and the active electrode 22.

Power for actuating the relay coils 44 and 46 is supplied by a photovoltaic cell 58. A lead 59 connects the photovoltaic cell 58 to the relay coils 44 and 46. A lead 61 connects the photovoltaic cell 58 to ground and to the shield 41. Capacitors 63 and 64 are connected between the lead 34 and the leads 38 and 61, respectively, and permit radiofrequency current which may reach the leads 34 and 38 to return to ground without passing through the photovoltaic cell 58 and the relay coils 44 and 46. The radiofrequency inductances 47 and 48 prevent such radiofrequency current passing through the photovoltaic cell 58 and the sensitive relay coils 44 and 46.

The photovoltaic cell 58 can be illuminated by an appropriate lamp 66, which can be powered by leads 69 and 71. The leads 69 and 71 can be connected to an appropriate portion of the circuitry of the radiofrequency generator to provide the necessary voltage to operate the lamp 66. The photovoltaic cell 58 can be designed to have an output of 0.6 volts D.C. and a current of 60 milliamperes. Such a cell can operate a sensitive relay such as a Potter-Brumfield relay MDP-2109. The lamp 66 can be a low voltage annunciator incandescent tungsten filament lamp such as a Sylvania 6RB or 12RB annunciator lamp. Such a lamp, when operated at 50% of full output rating, has a very long life and supplies sufficient radiant energy to optically saturate the photovoltaic cell.

The voltage at the contacts of the switch operating push buttons 32 and 36 is limited by the characteristics of the photovoltaic cell 58 and cannot exceed the output voltage of the photovoltaic cell 58 at optical saturation, which can be sufficiently low that there is no substantial danger of radiofrequency burns to the operator at the push buttons. The switching leads 34 and 38 are isolated from the active power lead 16 by the shield 18 of the coaxial cable which surrounds the active power lead 16 and the shield 41 surrounding the switching leads 34 and 38 to prevent leakage of radiofrequency current between the active power lead 16 and the switching leads 34 and 38.

The switch operating circuit illustrated in the drawing and described above is subject to modification without departing from the spirit and scope of the appended claims.

Having described my invention, what I claim as new and desire to secure by letters patent is:

1. A control circuit for a radiofrequency electrosurgical device including a radiofrequency generator, a handpiece, an active electrode means supported on the handpiece, and switch means mounted in the handpiece which comprises photovoltaic cell means and relay means connected in series with the switch means, means for illuminating the photovoltaic cell means, whereby closing of contacts of the switch means causes acturation of the relay means, and means connected to the relay means for causing the radiofrequency generator to power the active electrode, voltage at the switch means being limited by the voltage produced by the photovoltaic cell means.

2. A control circuit as in claim 1 wherein there is an active power lead powered by the radiofrequency generator and connected to the handpiece to power the active electrode, switch lead means connecting the switch means with the relay means and the photovoltaic cell, and an electrical shield separating the active power lead from the switch lead means.

3. A control circuit as in claim 2 wherein the electrical shield surrounds the active power lead.

4. A control circuit as in claim 2 wherein the electrical shield surrounds the switch lead means.

5. A control circuit as in claim 2 wherein the electrical shield includes first shield means surrounding the active power lead and second shield means surrounding the switch lead means.

6. A control circuit as in claim 1 wherein there is radiofrequency inductance means in series with the switch means, the relay means, and the photovoltaic cell to protect the photovoltaic cell and the relay means from radiofrequency current.

7. A control circuit as in claim 1 wherein there is switch lead means connecting the switch means with the relay means and the photovoltaic cell and there is capacitor means coupling the switch lead means to ground to direct radiofrequency current from the photovoltaic cell and the relay means.

8. A control circuit for an electrical device including a handpiece and switch means mounted in the handpiece which comprises photovoltaic cell means and relay means connected in series with the switch means, means for illuminating the photovoltaic cell means, whereby closing of contacts of the switch means causes actuation of the relay means, and means connected to the relay means for causing actuation of the electrical device, voltage at the switch means being limited by the voltage produced by the photovoltaic cell means.

* * * * *

UNITED STATES PATENT AND TRADEMARK OFFICE
CERTIFICATE OF CORRECTION

PATENT NO. : 4,123,673
DATED      : October 31, 1978
INVENTOR(S) : Donald I. Gonser It is certified that error appears in the above—identified patent and that said Letters Patent are hereby corrected as shown below:

Column 3, line 32, "actura-" should be -- actua- --.

*Signed and Sealed this*

*Twenty-seventh* Day of *February 1979*

[SEAL]

Attest:

RUTH C. MASON
*Attesting Officer*

DONALD W. BANNER
*Commissioner of Patents and Trademarks*